United States Patent
Malamas et al.

(12)

(10) Patent No.: US 6,214,842 B1
(45) Date of Patent: Apr. 10, 2001

(54) AMINO-THIAZOLIDINEDIONES USEFUL IN THE TREATMENT OF INSULIN RESISTANCE AND HYPERGLYCEMIA

(76) Inventors: Michael S. Malamas, 2443 Oleander Cir., Jamison, PA (US) 18929; Iwan Gunawan, 59 15th St., Somerset, NJ (US) 08873

( * ) Notice: Subject to any disclaimer, the term of this patent is extended or adjusted under 35 U.S.C. 154(b) by 0 days.

(21) Appl. No.: 09/568,832

(22) Filed: May 11, 2000

Related U.S. Application Data

(60) Provisional application No. 60/219,327, filed on May 12, 1999.

(51) Int. Cl.[7] ............... A61K 31/56; C07D 215/16; C07D 277/36
(52) U.S. Cl. ............... 514/314; 514/369; 546/178; 546/180; 548/183
(58) Field of Search ............... 514/314, 369; 546/178, 180; 548/183

(56) References Cited

U.S. PATENT DOCUMENTS

| 4,340,605 | 7/1982 | Kawamatsu | 548/183 |
|---|---|---|---|
| 4,997,948 | 3/1991 | Zask | 548/183 |
| 5,925,656 | * 7/1999 | Kallam . | |
| 6,133,295 | * 10/2000 | Ikeda . | |

FOREIGN PATENT DOCUMENTS 3045059   12/1981  (DE) .

OTHER PUBLICATIONS

Delgado et al., Wilson and Gisvold's Textbook of Organic Medical and Pharmaceutical Chemistry, 9th Ed., 1991, p. 30–31.
Fujita et al., Diabetes, 32, 1983, 804–810.

* cited by examiner

*Primary Examiner*—D. Margaret Seaman
(74) *Attorney, Agent, or Firm*—Arnold S. Milowsky

(57) ABSTRACT

This invention provides compounds of Formula I having the structure

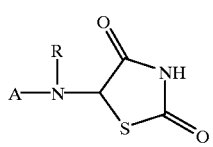

I wherein:

R is hydrogen or alkyl of 1–6 carbon atoms;

A is

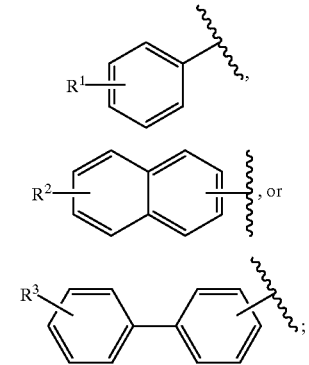

$R^1$, $R^2$, $R^3$ are each, independently, hydrogen, alkoxy of 1–6 carbon atoms, thioalkyl of 1–6 carbon atoms, trifluoromethyl,

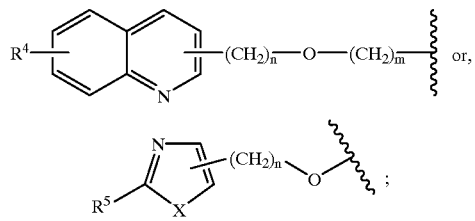

$R^4$ is hydrogen, alkyl of 1–6 carbon atoms, halogen, or alkoxy of 1–6 carbon atoms;

$R^5$ is phenyl, naphthyl, thienyl, furyl, wherein $R^5$ may be optionally mono-, di-, or tri-substituted with a sustituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —$CO_2H$, alkylcarbonyloxy of 2–7 carbon atoms, and alkylcarbonyl of 2–7 carbon atoms;

m=1–4;

n=1–4; and

X=O, S, or a pharmaceutically acceptable salt thereof, which are useful in treating metabolic disorders related to insulin resistance or hyperglycemia.

6 Claims, No Drawings

AMINO-THIAZOLIDINEDIONES USEFUL IN THE TREATMENT OF INSULIN RESISTANCE AND HYPERGLYCEMIA

This application claims the benefit of U.S. Provisional Application No. 60/219,327, which was converted from U.S. patent application Ser. No.09/310,828, filed May 12, 1999, pursuant to a petition filed under 37 C.F.R. 1.53(c)(2)(i).

BACKGROUND OF THE INVENTION

Diabetes mellitus is a syndrome characterized by abnormal insulin production, increased urinary output and elevated blood glucose levels. There are two major subclasses of diabetes mellitus. One is the insulin-dependent diabetes mellitus (IDDM or Type I), formerly referred to as juvenile onset diabetes since it was evident early in life, and non-insulin dependent diabetes mellitus (NIDDM or Type II), often referred to as maturity-onset diabetes. Exogenous insulin by injection is used clinically to control diabetes but suffers from several drawbacks. Insulin is a protein and thus cannot be taken orally due to digestion and degradation but must be injected. It is not always possible to attain good control of blood sugar levels by insulin administration. Insulin resistance sometimes occurs requiring much higher doses of insulin than normal. Another shortcoming of insulin is that while it may control hormonal abnormalities, it does not always prevent the occurrence of complications such as neuropathy, retinopathy, glomerulosclerosis, or cardiovascular disorders.

Orally effective antihyperglycemic agents are used to reduce blood glucose levels and to reduce damage to the nervous, retinal, renal or vascular systems through mechanisms affecting glucose metabolism. Such agents act in a variety of different mechanisms including inhibition of fatty acid oxidation, a-glycosidase inhibition, antagonism of $a_2$-receptors and inhibition of gluconeogenesis. Two classes of compounds have predominated: the biguanides as represented by phenformin and the sulfonylureas as represented by tolbutamide (Orinase®). A third class of compounds which has shown antihyperglycemic activity are thiazolidinediones of which ciglitazone is the prototype. Ciglitazone suppresses the symptoms of diabetes—hyperglycemia, hypertriglyceridemia and hyperinsulinemia [Diabetes 32, 804–10 (1983)]. Rezulin, a member of the thiazolidinediones, has recently been used successfully in the treatment of type II diabetes mellitus.

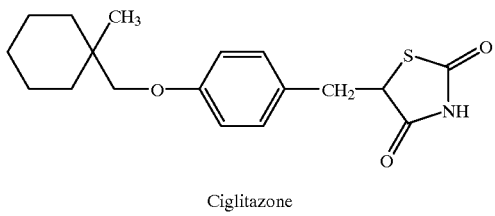

Ciglitazone

DESCRIPTION OF THE INVENTION

This invention provides a compound of formula I having the structure

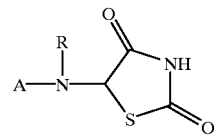

I wherein:
R is hydrogen or alkyl of 1–6 carbon atoms;
A is

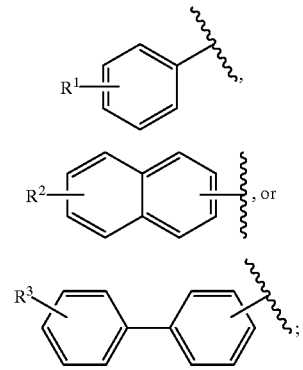

$R^1$, $R^2$, $R^3$ are each, independently, hydrogen, alkoxy of 1–6 carbon atoms, thioalkyl of 1–6 carbon atoms, trifluoromethyl,

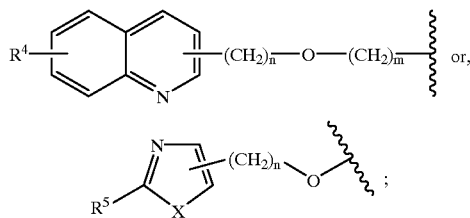

$R^4$ is hydrogen, alkyl of 1–6 carbon atoms, halogen, or alkoxy of 1–6 carbon atoms;
$R^5$ is phenyl, naphthyl, thienyl, furyl, wherein $R^5$ may be optionally mono-, di-, or tri-substituted with a sustituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —$CO_2H$, alkylcarbonyloxy of 2–7 carbon atoms, and alkylcarbonyl of 2–7 carbon atoms;
m=1–4;
n=1–4; and
or a pharmaceutically acceptable salt thereof, which are useful in treating metabolic disorders related to insulin resistance or hyperglycemia.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, with the imidic acidic functionality of the thiazolidinedione moiety, and when a compound of this invention contains a carboxylate or phenolic moiety, or similar moiety capable of forming base addition salts.

Alkyl includes both straight chain as well as branched moieties. Halogen means bromine, chlorine, fluorine, and iodine.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers, as well as the racemic and resolved, enantiomerically pure R and S stereoisomers, as well as other mixtures of the R and S stereoisomers and pharmaceutically acceptable salts thereof.

Preferred compounds of this invention include:

5-{4-[2-(5-methyl-2-phenyl-oxazol-4-yl)-ethoxy]-phenylamino}-thiazolidine-2,4-dione;
5-[(4-methoxyphenyl)amino]-thiazolidine-2,4-dione;
5-[[(4-methylthio)phenyl]amino]-thiazolidine-2,4-dione;
5-[(4-methoxyphenyl)methylamino]-thiazolidine-2,4-dione;
5-(2-naphthalenylamino)-thiazolidine-2,4-dione;
5-(4-chloro-naphthalen-1-ylamino)-thiazolidine-2,4-dione;
5-(1-naphthalenylamino)-thiazolidine-2,4-dione;
5-{3-[2-(5-ethyl -pyridin-2 -yl)-ethoxy]-phenylamino}-thiazolidine-2,4-dione;
5-{4'-[5-methyl-2-(4-trifluoromethyl-phenyl)-oxazol-4-ylmethoxy]-biphenyl-3-ylamino}-thiazolidine-2,4,-dione;
5-{3-[2-(quinolin-2-ylmethoxy)-ethyl]-phenylamino}-thiazolidine-2,4-dione;
5-{3-[naphthalen-2-ylmethoxy)-ethyl]-phenylamino}-thiazolidine-2,4-dione;
5-{3-[5-chloro-naphthalen-2-ylmethoxy)-ethyl]-phenylamino}-thiazolidine-2,4-dione;
5-{(5-[5-chloro-naphthalen-2-ylmethoxy)-ethyl]-naphthalen-2-ylamino}-thiazolidine-2,4-dione;

or a pharmaceutically acceptable salt thereof.

The compounds of this invention were be prepared according to the following schemes from commercially available starting materials or starting materials which can be prepared using literature procedures. These schemes show the preparation of representative compounds of this invention.

The invention compounds of Formula I may be prepared from intermediates of the formula II below wherein the variables A and R are as previously defined.

II

5-Amino-thiazolidinediones of Formula I are prepared from a Formula II intermediate by reacting with 5-bromo-thiazolidinedione in the presence of a base, i.e. triethylamine.

The amines of Formula II are either commercially available or can be prepared according to standard literature procedures as described in the following reaction schemes I–II.

Scheme I

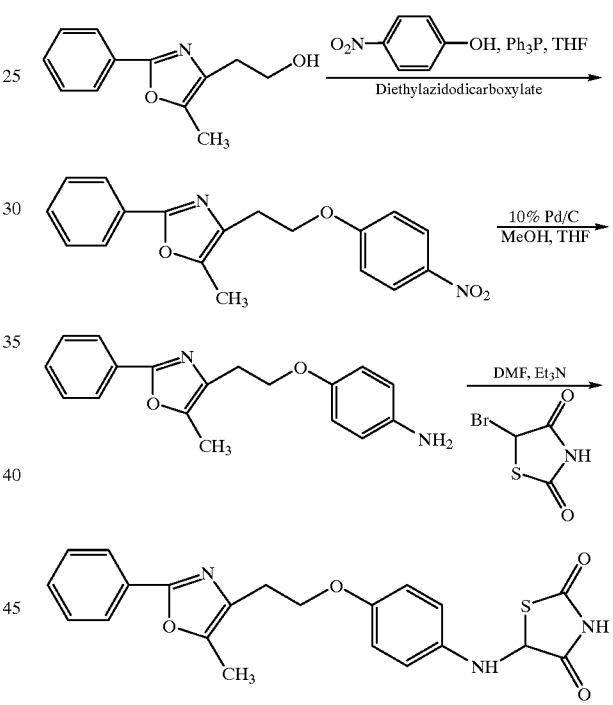

Scheme II

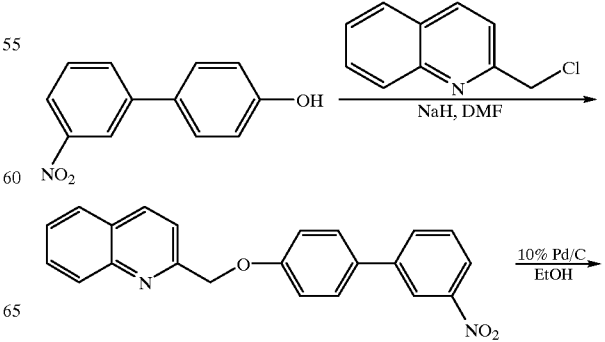

5
-continued

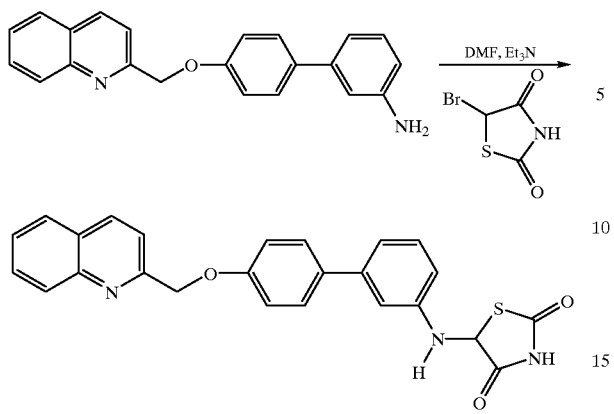

The starting oxazole intermediates can be prepared according to standard literature procedures. For example, 4-(1'-hydroxyethyl)-5-methyl-2-phenyl oxazoles and thiazoles can be prepared according to Scheme III (European Patent EP 0177353A2), and 2-phenyl-4-chloromethyl-5-methyloxazoles can be prepared by known methods conventional in the art Scheme IV (Heterocyclic Compounds 34, 1979, and Heterocyclic Compounds 45, 1986).

Scheme III

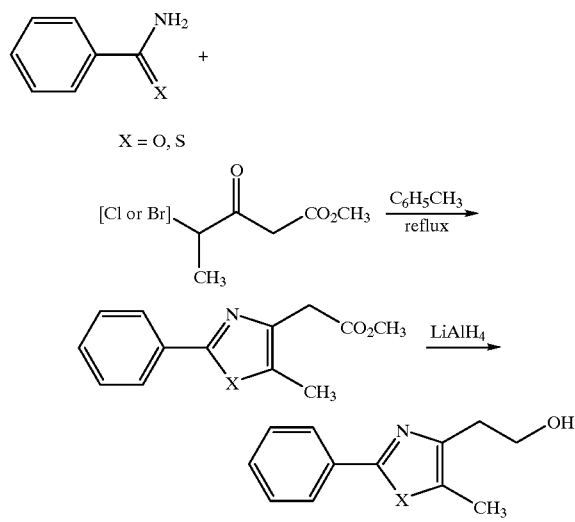

Scheme IV

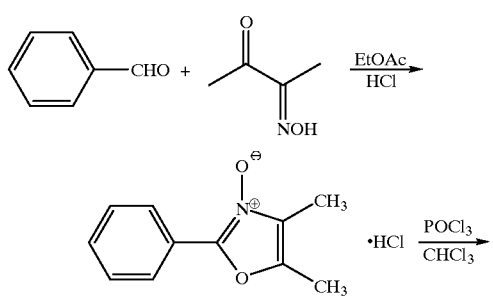

6
-continued

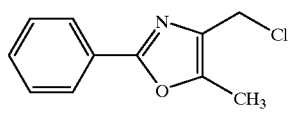

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedures.

Determination of Blood Glucose Lowering in db/db Mice

On the morning of Day 1, 35 mice [male diabetic db/db (C57BL/KsJ) mice (Jackson Laboratories), 2–7 months of age and 50–70 g] were fasted for 4 hours, weighed and a baseline blood sample (15–30 μl) was collected from the tail-tip of each mouse without anesthesia, and placed directly into a fluoride-containing tube, mixed and maintained on ice. Food was then returned to the mice. The plasma was an separated and levels of glucose in plasma determined by the Abbott VP Analyzer. Because of the variable plasma glucose levels of the db/db mice, 5 mice having the most extreme (i.e., highest or lowest) plasma glucose levels were excluded and the remaining 30 mice were randomly assigned into 7 groups of equivalent mean plasma glucose levels (N=6 for vehicle and N=4 for each drug group). On the afternoon of Days 1, 2 and 3, the vehicle, control or test drugs were administered (p.o.) to the ad libitum fed mice. On the morning of Day 4, the mice were weighed and food removed, but water was available ad libitum. Three hours later, a blood sample was collected and then the mice were given the fourth administration of drug or vehicle. Blood samples were collected again from the unanesthetized mice at 2 and 4 hrs after drug administration. The plasma was separated and levels of glucose in plasma was determined by the Abbott VP Analyzer.

For each mouse, the percent change of its plasma glucose level on Day 4 (mean of the 2 and 4 hr samples) from respective level before drug administration (Day 1 baseline sample) is determined as follows:

$$\frac{\text{mean of 2 and 4 hr samples (Day 4)}}{\text{Baseline Sample (Day 1)}} \times 100$$

Analysis of variance followed by Dunnett's multiple comparison (one-sided) will be used to estimate the degree of statistical significance of the difference between the vehicle control group and the individual drug-treated groups. A drug will be considered active, at the specific dosage administered, if the difference of the plasma glucose level has a p<0.05. The compound of Example 1 was active in this standard pharmacological test procedure with a 20 percent reduction of glucose at an oral dose of 100 mg/kg.

REFERENCES

1. Coleman, D. L. (1982) Diabetes-obesity syndromes in mice. Diabetes 31 (Suppl. 1); 1–6.
2. Tutwiler, G. F., T. Kirsch, and G. Bridi (1978). A pharmnacologic profile of McN-3495 [N-(1-methyl-2- pyrrolidinylidene)-N'-phenyl-11-pyrrolidine-carboximidamide], a new, orally effective hypoglycemic agent. Diabetes 27:856–857.
3. Lee, S. M., G. Tutwiler, R. Bressler, and C. H. Kircher (1982). Metabolic control and prevention of nephropathy by 2-tetradecylglycidate in the diabetic mouse (db/db). Diabetes 31:12–18.
4. Chang, A. Y., B. W. Wyse, B. J. Gilchrist, T. Peterson, and R. Diani (1983) Ciglitazone, a new hypoglycemic agent. 1. Studies in ob/ob and db/db mice, diabetic Chinese hamsters, and normal and streptozocin-diabetic rats. Diabetes 32: 830–838.
5. Hosokawa, T., K. Ando, and G. Tamura (1985). An ascochlorin derivative, AS-6, reduces insulin resistance in the genetically obese diabetic mouse, db/db. Diabetes 34: 267–274.

Determination of Blood Glucose Lowering Effect in ob/ob Mice

The non-insulin-dependent diabetic syndrome can be typically characterized by obesity, hyperglycemia, abnormal insulin secretion, hyperinsulinemia and insulin resistance. The genetically obese-hyperglycemic ob/ob mouse exhibits many of these metabolic abnormalities and is useful for evaluating hypoglycemic agents useful in treating NIDDM (Coleman, 1978).

Male or female ob/ob mice (C57B116J), ages 2 to 5 months (10 to 65 g), of a similar age are randomized according to plasma glucose into 4 groups of 10 mice. The mice are housed 5 per cage and are maintained on normal rodent chow with water ad libitum. The mice receive test compound daily. The test compound is suspended in 0.5 mL of 0.5% methyl cellulose and is administered by gavage (dissolved in drinking water) or admixed in the diet. The dose of compound given ranges from 2.5 to 200 mg/kg/day. Body weight of fed animals is measured at the beginning of each week and doses for the entire week are calculated using this weight and are expressed in terms of the active moiety of the compound. Control mice receive vehicle only.

On the morning of Days 4, 7 or 14 two drops of blood (approximately 50 pl) are collected into sodium fluoride containing tubes either from the tail vein or after decapitation. For those studies in which the compound is administered daily by gavage, the blood samples are collected four hour after compound administration. The plasma is isolated by centrifugation and the concentration of glucose is measured enzymatically on an Abbott V. P. Analyzer and the plasma concentration of insulin is determined by radioimmunoassay (Heding, 1972). For each mouse, the percentage change in plasma glucose on Day 4, 7 or 14 is calculated relative to the mean plasma glucose of the vehicle treated mice. Analysis of variance followed by Dunnett's Comparison Test (one tailed) is used to estimate the significant difference between the plasma glucose values from the control group and the individual compound treated groups. The actual difference between the mean percent change of the vehicle and drug-treated groups is exemplified with Example 9, where a 30 percent reduction of glucose was demonstrated with an oral dose of 200 mg/kg.

Based on the results obtained in these standard pharmacological test procedures, representative compounds of this invention have been shown to lower blood glucose levels and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at an oral daily dosage of from about 1 mg/kg to about 1000 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1

5-{4-[2-(5-Methyl-2-phenyl-oxazol-4-yl)-ethoxy]-phenylamino}-thiazolidine-2,4-dione Step a) 5-Methyl-4-[2-(4-nitrophenoxy)ethyl]-2-phenyl-oxazole Into a cold (0° C.) solution of 4-(2'-hydroxy-ethyl)-5-methyl-2-phenyloxazole (10 g, 49.26 mmol), triphenylphosphine (12.9 g, 49.26 mmol), 4-nitrophenol (6.85 g, 49.26 mmol) in THF (100 mL) was added dropwise diethylazodicarboxylate (7.75 mL, 49.26 mmol). The mixture was allowed to come to room temperature and stirred for 72 hours, poured into $H_2O$ and extracted with EtOAc. The organic extracts were dried over $MgSO_4$. Evaporation and purification by flash chromatography, on silica gel (hexane/EtOAc 3/1) gave a brown solid (14.5 g, 91% yield, m.p. 89–90° C.).

Analysis for: $C_{18}H_{16}N_2O_4$ Calc'd: C, 66.66; H, 4.97; N, 8.64. Found: C, 66.64; H, 4.96; N, 8.39.

Step b) 4-[2-(5-Methyl-2-phenyl-oxazol-4-yl)-ethoxyl]-aniline

A mixture of 5-methyl-4-[2-(4-nitrophenoxy)ethyl]-2-phenyl-oxazole (13.5 g, 41.67 mmol), methanol (100 mL), THF (50 mL) and 10% Pd/C (1.0 g) was stirred under hydrogen (50 psi) for 5 hours. The mixture was filtered through florisil and the filtrate was concentrated in vacuo to give an off-white solid (12.6 g, 98% yield, m.p. 86–87° C.).

Analysis for: $C_{18}H_{18}N_2O_2$ Calc'd: C, 73.45; H, 6.16; N, 9.52. Found: C, 73.37; H, 6.18; N, 9.17.

Step c) 5-{4-[2-(5-Methyl-2-phenyl-oxazol-4-yl)-ethoxyl]-phenylamino}-thiazolidine-24-dione Into a mixture of 4-[2-(5-methyl-2-phenyl-oxazol-4-yl)-ethoxy]-aniline (2.0 g, 6.8 mmol) 5-bromo-thiazolidine-2,4-dione (prepared according to reference J. Med. Chem. 1418–1423, 1990, 1.33 g, 6.8 mmol), and DMF (20 mL) was added triethylamine (0.94 mL, 6.8 mmol). The mixture was stirred for 20 minutes poured into water, acidified with HCl (2 N) and extracted with EtOAc. The organic extracts were dried over MgSO4. The crude product was recrystallized from acetone/ethyl ether/hexane to give a yellow solid (1.96 g, 70% yield, m.p. 179–180 ° C.).

Analysis for: $C_{21}H_{19}N_3O_4S$ Calc'd: C, 61.60; H, 4.68; N, 10.26. Found: C, 61.46; H, 4.67; N, 10.01.

EXAMPLE 2

5-[(4-Methoxyphenyl)amino]-thiazolidine-2,4-dione

The title compound was prepared in substantially the same manner as described in Example 1, and was obtained as a light brown solid, m.p. 180–181° C.

Analysis for: $C_{10}H_{10}N_2O_3S$ Calc'd: C, 50.41; H, 4.23; N, 11.76. Found: C, 50.40; H, 4.42; N, 11.66.

EXAMPLE 3

5-[[(4-Methylthio)phenyl]amino]-thiazolidine-2,4-dione

The title compound was prepared in substantially the same manner as described in Example 1, and was obtained as a light gray solid, m.p. 195–197° C.

Analysis for: $C_{10}H_{10}N_2O_2S_2$ Calc'd: C, 47.23; H, 3.96; N, 11.01. Found: C, 47.19; H, 4.00; N, 10.86.

EXAMPLE 4

5-[(4-Methoxyphenyl)methylamino]-thiazolidine-2,4-dione

The title compound was prepared in substantially the same manner as described in Example 1, and was obtained as a light gray solid, m.p. 140–142° C.

Analysis for: $C_{11}H_{12}N_2O_3S$ Calc'd: C, 52.37; H, 4.79; N, 11.10. Found: C, 52.23; H, 4.79; N, 11.16.

EXAMPLE 5

5-(2-Naphthalenylamino)-thiazolidine-2,4-dione

The title compound was prepared in substantially the same manner as described in Example 1, and was obtained as a white solid, m.p. 200–201° C.

Analysis for: $C_{13}H_{10}N_2O_2S$ Calc'd: C, 60.45; H, 3.90; N, 10.85. Found: C, 60.55; H, 3.88; N, 10.80.

EXAMPLE 6

5-(1-Naphthalenylamino)-thiazolidine-2,4-dione

The title compound was prepared in substantially the same manner as described in Example 1, and was obtained as a light tan solid, m.p. 195–197° C.

Analysis for: $C_{13}H_{10}N_2O_2S$ Calc'd: C, 60.45; H, 3.90; N, 10.85. Found: C, 60.07; H, 3.90; N, 10.74

EXAMPLE 7

5-(4-Bromo-naphthalen-1-ylamino)-thiazolidine-2,4-dione

The title compound was prepared in substantially the same manner as described in Example 1, and was obtained as an off white solid, m.p. 199–200° C.

Analysis for: $C_{13}H_9BrN_2O_2S$ Calc'd: C, 46.30; H, 2.69; N, 8.31. Found: C, 46.24; H, 2.67; N, 8.15.

EXAMPLE 8

5-(4-Chloro-naphthalen-1-ylamino)-thiazolidine-2,4-dione

The title compound was prepared in substantially the same manner as described in Example 1, and was obtained as a light purple solid, m.p. 205–206° C.

Analysis for: $C_{13}H_9ClN_2O_2S$ Calc'd: C, 53.34; H, 3.10; N, 9.57. Found: C, 53.26; H, 3.02; N, 9.45.

EXAMPLE 9

5-(1-Naphthalenylamino)-thiazolidine-2,4-dione

The title compound was prepared in substantially the same manner as described in Example 1, and was obtained as a light tan solid, m.p. 195–197° C.

Analysis for: $C_{13}H_{10}N_2O_2S$ Calc'd: C, 60.45; H, 3.90; N, 10.85. Found: C, 60.07; H. 3.90; N, 10.74

EXAMPLE 10

5-{3-[2-(5-Ethyl-pyridin-2-yl)-ethoxy]-phenylamino}-thiazolidine-2,4-dione

The title compound was prepared in substantially the same manner as described in Example 1, and was obtained as an off-white solid, m.p. 140–142° C.

Analysis for: $C_{18}H_{19}N_3O_3S$ Calc'd: C, 60.49; H, 5.36; N, 11.76. Found: C, 60.06; H, 5.31; N, 11.65.

EXAMPLE 11

5-[4'-(Quinolin-2-ylmethoxy)-biphenyl-3-ylamino]-thiazolidine-2,4-dione

Step a) 2-(3'-Nitro-biphenyl-4-yloxymethyl)-guinoline

Sodium hydride (0.33 g, 8.4 mmol) was added dropwise into a cold (0° C.) solution of 4-(3-nitrophenyl)phenol (1.5 g, 6.07 mmol) in DMF (25 mL). The mixture was stirred for 20 minutes at 0° C. and 20 minutes at room temperature, and then 2-chloromethylquinoline (1.3 g, 7.7 mmol) in DMF (15 mL) was added at once. The mixture was stirred at room temperature for 12 hours, poured into water and extracted with EtOAc. The organic extracts were dried over $MgSO_4$. Evaporation and purification by flash chromatography (hexane/EtOAc 5/1) gave a yellow solid (0.9 g 49% yield, m.p. 115–116 ° C.).

Analysis for: $C_{22}H_{16}N_2O_3$ Calc'd: C, 74.15; H, 4.52; N, 7.86. Found: C, 74.15; H, 4.47; N, 7.97.

Step b) 4'-(Quinolin-2-ylmethoxy)-biphenyl-3-ylamine

The title compound was prepared in substantially the same manner as described in Example 1, step b, and was obtained as an off-white solid, m.p. 132–133° C.

Analysis for: $C_{22}H_{18}N_2O$ Calc'd: C, 80.96; H, 5.56; N, 8.58. Found: C, 80.97; H, 5.57; N, 8.24.

Step c) 5-[4'-(Quinolin-2-ylmethoxy)-biphenyl-3-ylamino]-thiazolidine-2,4-dione

The title compound was prepared in substantially the same manner as described in Example 1, step c, and was obtained as a white solid, m.p. 162–163° C.

Analysis for: $C_{25}H_{19}N_3O_3S$ Calc'd: C, 68.01; H, 4.34; N, 9.52. Found: C, 67.46; H, 4.09; N, 89.42.

EXAMPLE 12

5-{4'-[5-Methyl-2-(4-trifluoromethyl-phenyl)-oxazol-4-ylmethoxy]-biphenyl-3-ylamino}-thiazolidine-2,4,-dione The title compound was prepared in substantially the same manner as described in Example 2, and was obtained as an off-white solid, m.p. 190–191° C.

Analysis for: $C_{27}H_{20}F_3N_3O_4S$ Calc'd: C, 60.11; H, 3.74; N, 7.79. Found: C, 59.41; H, 3.60; N, 7.63.

EXAMPLE 13

5-{3-[2-(Quinolin-2-ylmethoxy)-ethyl]-phenylamino}-thiazolidine-2,4-dione

The title compound was prepared in substantially the same manner as described in Example 2, and was obtained as a light yellow solid, m.p. 167–168° C.

Analysis for: $C_{21}H_{19}N_3O_3S$ Calc'd: C, 64.11; H, 4.87; N, 10.68. Found: C, 64.17; H, 4.95; N, 10.13.

EXAMPLE 14

5-{3-[Naphthalen-2-ylmethoxy)-ethyl]-phenylamino}-thiazolidine-2,4-dione

The title compound was prepared in substantially the same manner as described in Example 1, and was obtained as a white solid, m.p. 105–106° C.

Analysis for: $C_{22}H_{20}N_2O_3S$ Calc'd: C, 67.33; H, 5.14; N, 7.14. Found: C, 66.79; H, 5.10; N, 7.14.

EXAMPLE 15

5-{3-[5-Chloro-naphthalen-2-ylmethoxy)-ethyl]-phenylamino}-thiazolidine-2,4-dione The title compound was prepared in substantially the same manner as described in Example 1, and was obtained as a white solid, m.p. 65–66° C.

Analysis for: $C_{22}H_{19}ClN_2O_3S$ Calc'd: C, 61.89; H, 4.49; N, 6.56. Found: C, 61.67; H, 4.54; N, 6.18.

EXAMPLE 16

5-{5-[5-Chloro-naphthalen-2-ylmethoxy)-ethyl]-naphthalen-2-ylamino}-thiazolidine-2,4-dione The title compound was prepared in substantially the same manner as described in Example 1, and was obtained as aa off-white solid, m.p. 175–176° C.

Analysis for: $C_{223}H_{17}N_3O_3S$ Calc'd: C, 66.49; H, 4.12; N, 10.11. Found: C, 66.76; H, 4.01; N, 9.92.

What is claimed is:

1. A compound of formula I having the structure

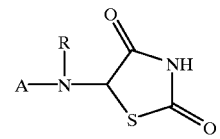

I wherein:

R is hydrogen or alkyl of 1–6 carbon atoms;

A is

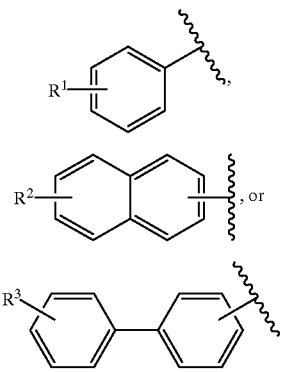

$R^1$, $R^2$, $R^3$ are each, independently, hydrogen, alkoxy of 1–6 carbon atoms, thioalkyl of 1–6 carbon atoms, trifluoromethyl,

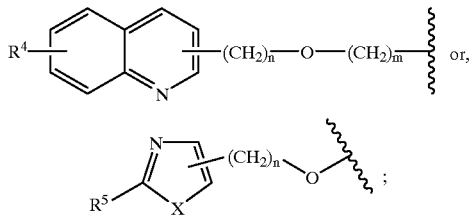 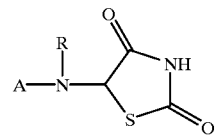

R⁴ is hydrogen, alkyl of 1–6 carbon atoms, halogen, or alkoxy of 1–6 carbon atoms;

R⁵ is phenyl, naphthyl, thienyl, furyl, wherein R⁵ may be optionally mono-, di-, or tri-substituted with a sustituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —CO₂H, alkylcarbonyloxy of 2–7 carbon atoms, and alkylcarbonyl of 2–7 carbon atoms;

m=1–4;

n=1–4; and

X=O, S, or a pharmaceutically acceptable salt thereof.

2. The compound according to claim 1, which is a) {4-[2-(5-methyl-2-phenyl-oxazol-4-yl)-ethoxy]-phenylamino}-thiazolidine-2,4-dione;
b) 5-[(4-methoxyphenyl)amino]-thiazolidine-2,4-dione;
c) 5-[[(4-methylthio)phenyl]amino]-thiazolidine-2,4-dione;
d) 5-[(4-methoxyphenyl)methylamino]-thiazolidine-2,4-dione;
e) 5-(2-naphthalenylamino)-thiazolidine-2,4-dione;
f) 5-(1-naphthalenylamino)-thiazolidine-2,4-dione;
g) 5-(4-bromo-naphthalen-1-ylamino)-thiazolidine-2,4-dione;
h) 5-(4-chloro-naphthalen-1-ylamino)-thiazolidine-2,4-dione;
i) 5-(1-naphthalenylamino)-thiazolidine-2,4-dione;
j) 5-{3-[2-(5-ethyl-pyridin-2-yl)-ethoxy]-phenylamino}-thiazolidine-2,4-dione;
k) 5-[4'-(quinolin-2-ylmethoxy)-biphenyl-3-ylamino]-thiazolidine-2,4-dione;
l) 5-{4'-[5-methyl-2-(4-trifluoromethyl-phenyl)-oxazol-4-ylmethoxy]-biphenyl-3-ylamino}-thiazolidine-2,4,-dione;
m) 5-{3-[2-(quinolin-2-ylmethoxy)-ethyl]-phenylamino}-thiazolidine-2,4-dione;
n) 5-{3-[naphthalen-2-ylmethoxy)-ethyl]-phenyl amino}-thiazolidine-2,4-dione;
o) 5-{3-[5-chloro-naphthalen-2-ylmethoxy)-ethyl]-phenylamino}-thiazolidine-2,4-dione; or
p) 5-{5-[5-chloro-naphthalen-2-ylmethoxy)-ethyl]-naphthalen-2-ylamino}-thiazolidine-2,4-dione;

or a pharmaceutically acceptable salt thereof.

3. A method of treating metabolic disorders mediated by insulin resistance or hyperglycemia in a mammal in need thereof which comprises administering to said mammal, a compound of formula I having the structure wherein:

R is hydrogen or alkyl of 1–6 carbon atoms;

A is

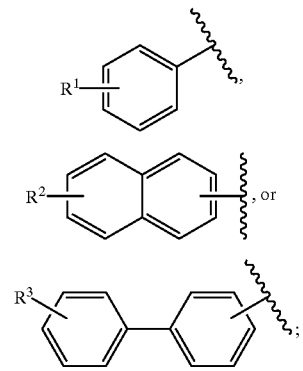

R¹, R², R³ are each, independently, hydrogen, alkoxy of 1–6 carbon atoms, thioalkyl of 1–6 carbon atoms, trifluoromethyl,

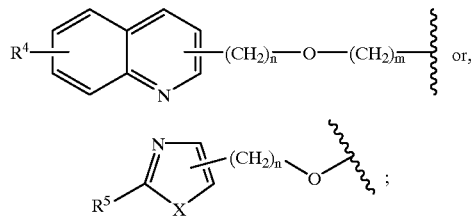

R⁴ is hydrogen, alkyl of 1–6 carbon atoms, halogen, or alkoxy of 1–6 carbon atoms;

R⁵ is phenyl, naphthyl, thienyl, furyl, wherein R⁵ may be optionally mono-, di-, or tri-substituted with a sustituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —CO₂H, alkylcarbonyloxy of 2–7 carbon atoms, and alkylcarbonyl of 2–7 carbon atoms;

m=1–4;

n=1–4;and

X=O, S, or a pharmaceutically acceptable salt thereof.

4. A method of treating or inhibiting type II diabetes in a mammal in need thereof which comprises administering to said mammal, a compound of formula I having the structure

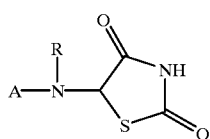

wherein:

R is hydrogen or alkyl of 1–6 carbon atoms;

A is

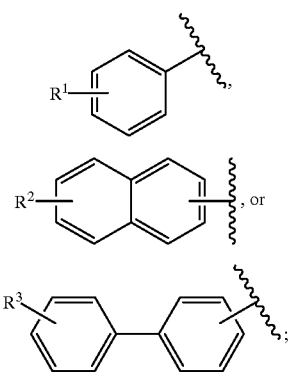

R¹, R², R³ are each, independently, hydrogen, alkoxy of 1–6 carbon atoms, thioalkyl of 1–6 carbon atoms, trifluoromethyl,

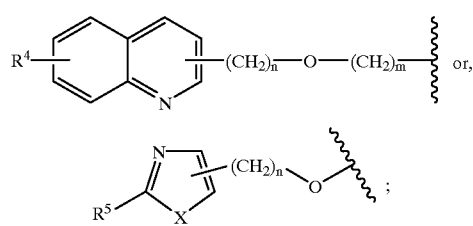

R⁴ is hydrogen, alkyl of 1–6 carbon atoms, halogen, or alkoxy of 1–6 carbon atoms;

R⁵ is phenyl, naphthyl, thienyl, furyl, wherein R⁵ may be optionally mono-, di-, or tri-substituted with a sustituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —CO₂H, alkylcarbonyloxy of 2–7 carbon atoms, and alkylcarbonyl of 2–7 carbon atoms;

m=1–4;

n=1–4; and

X=O, S, or a pharmaceutically acceptable salt thereof.

5. A method of modulating glucose levels in a mammal in need thereof which comprises administering to said mammal, a compound of formula I having the structure

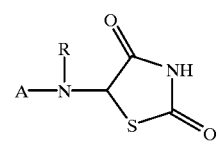

wherein:

R is hydrogen or alkyl of 1–6 carbon atoms;

A is

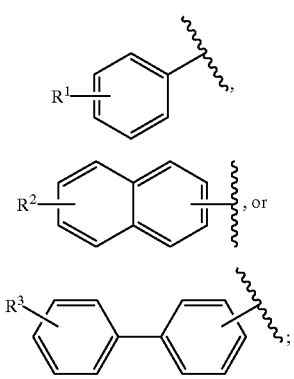

R¹, R², R³ are each, independently, hydrogen, alkoxy of 1–6 carbon atoms, thioalkyl of 1–6 carbon atoms, trifluoromethyl,

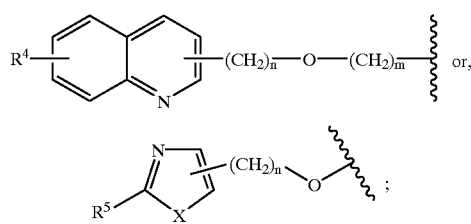

R⁴ is hydrogen, alkyl of 1–6 carbon atoms, halogen, or alkoxy of 1–6 carbon atoms;

R⁵ is phenyl, naphthyl, thienyl, furyl, wherein R5 may be optionally mono-, di-, or tri-substituted with a sustituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —CO₂H, alkylcarbonyloxy of 2–7 carbon atoms, and alkylcarbonyl of 2–7 carbon atoms;

m=1–4;

n=1–4; and

X=O, S, or a pharmaceutically acceptable salt thereof.

6. A pharmaceutical composition which comprises a compound of formula I having the structure

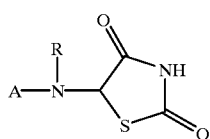

wherein:

R is hydrogen or alkyl of 1–6 carbon atoms;

A is

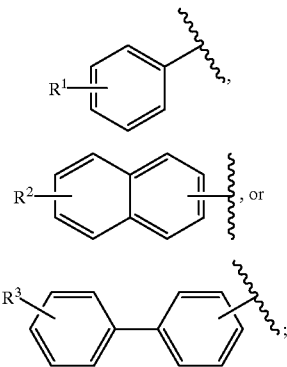

$R^1$, $R^2$, $R^3$ are each, independently, hydrogen, alkoxy of 1–6 carbon atoms, thioalkyl of 1–6 carbon atoms, trifluoromethyl,

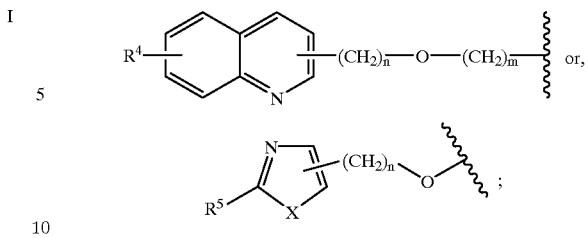

$R^4$ is hydrogen, alkyl of 1–6 carbon atoms, halogen, or alkoxy of 1–6 carbon atoms;

$R^5$ is phenyl, naphthyl, thienyl, furyl, wherein $R^5$ may be optionally mono-, di-, or tri-substituted with a sustituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —$CO_2H$, alkylcarbonyloxy of 2–7 carbon atoms, and alkylcarbonyl of 2–7 carbon atoms;

m=1–4;

n=1–4; and

X=O, S, or a pharmaceutically acceptable salt thereof, and a pharmaceutical carrier.

* * * * *